United States Patent
Zhang et al.

(10) Patent No.: US 9,840,462 B2
(45) Date of Patent: Dec. 12, 2017

(54) SOLVENT REFINING METHOD FOR ISOCYANATE PREPARED BY PHOSGENE METHOD AND DEVICES USED IN SAME

(71) Applicant: Wanhua Chemical Group Co., Ltd., Yantai (CN)

(72) Inventors: Hongke Zhang, Yantai (CN); Yu Yao, Yantai (CN); Dongke Zhao, Yantai (CN); Weiqi Hua, Yantai (CN); Bin Chen, Yantai (CN); Dekai Shi, Yantai (CN); Qinglong Chen, Yantai (CN); Dan Xu, Yantai (CN); Yang Wang, Yantai (CN); Qile Shi, Yantai (CN)

(73) Assignee: Wanhua Chemical Group Co., Ltd. (CN)

( * ) Notice: Subject to any disclaimer, the term of this patent is extended or adjusted under 35 U.S.C. 154(b) by 0 days.

(21) Appl. No.: 15/301,132

(22) PCT Filed: Apr. 11, 2014

(86) PCT No.: PCT/CN2014/075169
§ 371 (c)(1),
(2) Date: Sep. 30, 2016

(87) PCT Pub. No.: WO2015/149381
PCT Pub. Date: Oct. 8, 2015

(65) Prior Publication Data
US 2017/0022152 A1 Jan. 26, 2017

(30) Foreign Application Priority Data
Apr. 1, 2014 (CN) .......................... 2014 1 0128614

(51) Int. Cl.
*C07C 263/00* (2006.01)
*C07C 263/20* (2006.01)
*C07C 263/10* (2006.01)
*B01D 15/00* (2006.01)
*B01D 15/10* (2006.01)

(52) U.S. Cl.
CPC ............ *C07C 263/20* (2013.01); *B01D 15/00* (2013.01); *B01D 15/10* (2013.01); *C07C 263/10* (2013.01)

(58) Field of Classification Search
CPC .............................. C07C 263/20; B01D 15/00
USPC ........................................................ 560/353
See application file for complete search history.

(56) References Cited

U.S. PATENT DOCUMENTS

| | | |
|---|---|---|
| 3,953,324 A | 4/1976 | Deal et al. |
| 5,362,399 A | 11/1994 | Schwarz et al. |
| 7,524,405 B2 | 4/2009 | Sohn et al. |
| 7,584,629 B2 | 9/2009 | Sohn et al. |
| 7,767,178 B2 | 8/2010 | Hilaly et al. |
| 8,759,569 B2 | 6/2014 | Schelling et al. |

FOREIGN PATENT DOCUMENTS

| | | | | |
|---|---|---|---|---|
| CN | 1729169 | A | | 2/2006 |
| CN | 1729170 | A | | 2/2006 |
| CN | 1903990 | A | | 1/2007 |
| CN | 101108296 | A | | 1/2008 |
| CN | 101326495 | A | | 12/2008 |
| CN | 101671277 | A | * | 3/2010 |
| CN | 101698652 | A | * | 4/2010 |
| CN | 101703869 | A | | 5/2010 |
| CN | 101870666 | A | | 10/2010 |
| CN | 101955426 | A | | 1/2011 |
| CN | 102482205 | A | | 5/2012 |
| CN | 103073412 | A | | 5/2013 |
| DE | CN 1729170 | A | * | 2/2006 ........... C07C 263/20 |
| GB | 848986 | A | * | 9/1960 |

OTHER PUBLICATIONS

International Search Report for Application No. PCT/CN2014/075169 dated Jan. 15, 2015.

* cited by examiner

Primary Examiner — Deborah D Carr
(74) Attorney, Agent, or Firm — Lerner, David, Littenberg, Krumholz & Mentlik, LLP

(57) ABSTRACT

A solvent refining method for isocyanate prepared by the phosgene method and multistage absorbing towers used in same. Solvent to be refined which contains water, iron, and/or phosgene, hydrogen chloride and other materials with color is dealt by the present method and multistage absorbing towers, which can effectively prevent a drying agent from absorbing water and hardening, partial overheating in the tower and generating channeling. Meanwhile, the pressure drop is effectively lowered. In addition, the content of water is ≤50 ppm, the content of iron is ≤5 ppm, the content of phosgene and hydrogen chloride is ≤20 ppm, Pt—Co chroma is ≤20 in the refined solvent. Therefore, the refined solvent can be used as the solvent for preparing isocyanate in the phosgene method and remarkably improve an L color of isocyanate.

22 Claims, 1 Drawing Sheet

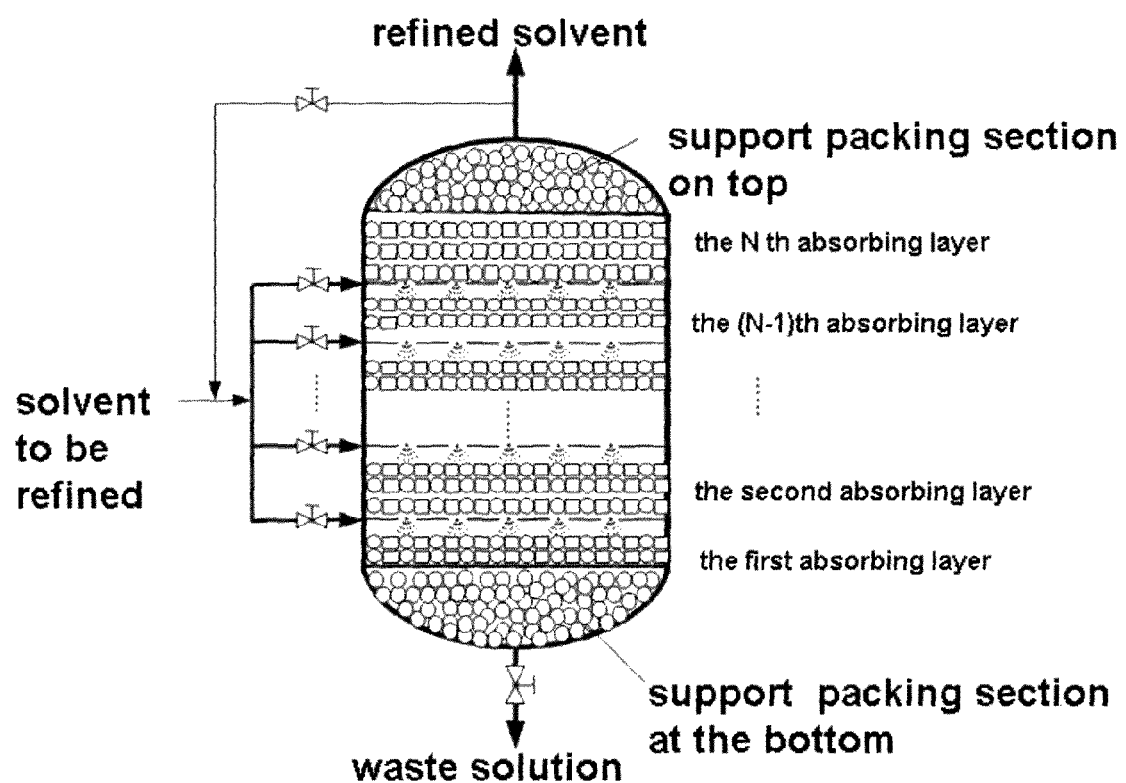

SOLVENT REFINING METHOD FOR ISOCYANATE PREPARED BY PHOSGENE METHOD AND DEVICES USED IN SAME

CCROSS-REFERENCE TO RELATED APPLICATIONS

The present application is a national phase entry under 35 U.S.C. §371 of International Application No. PCT/CN2014/075169, filed Apr. 11, 2014, which claims priority from Chinese Patent Application No. 201410128614.8 filed Apr. 1, 2014, all of which are hereby incorporated herein by reference.

TECHNICAL FIELD

The present invention belongs to the field of chemical industry, specifically, it related to a solvent refining method for isocyanates prepared by the phosgene method and devices used in same, and especially it relates to a method of rapid removing the water content, the iron content, the phosgene and hydrogen chloride in the solvent used in the manufacture of isocyanates by the phosgene method and decreasing the color number of the solvent.

TECHNICAL BACKGROUND

At present, both at home and abroad, isocyanates, including MDI (Diphenylmethane diisocyanate), TDI (toluene diisocynate), HDI (hexamethylene diisocyanate) etc., are prepared mainly by the phosgene method. Said method is to mix polyamine such as diphenyl methane diamine, polymethylene polyphenyl polyamine or toluene diamine with solvents, and then sufficiently to mix with phosgene to carry out the phosgenation reaction, the corresponding phosgenation reaction liquid is obtained after the end of the reaction, and the crude products are obtained after the removal of the phosgene and solvents from the phosgenation reaction liquid. In said reaction, chlorobenzene, o-dichlorobenzene, toluene etc. are mainly used as solvents.

The solvents used during the manufacturing process of isocyanates, have very high requirements for water content, iron component, phosgene content, hydrogen chloride content and the Pt—Co color number; generally, it is required that the content of water is lower than 100 ppm, the content of iron is lower than 5 ppm, the content of phosgene and hydrogen chloride is lower than 50 ppm, and the color number of Pt—Co is lower than 30. If the content of water in the solvent is too high, in one aspect, the corrosion of the devices will be accelerated under the presence of phosgene, in another aspect, and the water will react with isocyanates to produce urea, which will seriously influence the quality of the products. If the content of iron is too high in the solvent, then the content of iron in the isocyanate products will be too high, thus influencing the foaming quality of the products. If the content of phosgene and hydrogen chloride is too high, the corrosion of the devices will be accelerated, and isocyanates will be produced by the reaction of polyamine and phosgene during the mixing of the solvent and polyamine, and then urea will be produced by reacting the isocyanates with polyamine, which will also influence the quality of the products. In addition, if the colour number of the solvent is high, the color of the isocyanate products will be influenced.

In the industrialized production of isocyanates, during the startup of the overhaul of the devices, at first, solvents are used to run the system to bring the water content out, and to generate waste solvents with high color number and high water content, and during the abnormal startup and shutdown of the devices, some waste solvents that contains phosgene and hydrogen chloride will also be generated. If these waste solvents are drained directly, it will generate a huge amount of waste liquid and a waste of resources. Therefore, because of economical and environmental reasons, the issue of the recovery and reuse of the waste solvents should be studied. In addition, during the manufacturing process of isocyanates, the solvents will be lost, and fresh solvents need to be added in the reaction system. However, the solvents that are commercially available usually contains a high amount of water, iron etc., which are not beneficial to the production of isocyanates or the color number of the solvents is too high. Therefore, the disposing of the fresh solvents shall also be studied.

Patent document CN103073412A discloses a dehydration system and the dehydration process thereof for the PTA (purified terephthalic acid) solvent. In said document, it is described that the water content in PTA solvent is removed by extracting and azeotropic rectification, and the load and the amount of steam of the subsequent azeotropic rectification can be reduced. But for the solvents that contain lower amount of water (lower than 100 ppm) and the solvents that contain iron, the effect is actually modest, and the entrainer will influence the quality of the isocyanate products.

Patent document CN101955426A discloses a optimized method for the dehydrating process of the azeotropic rectification solvent of industrial purified terephthalic acid device, which provides base and basis to improvement of production process, energy conservation, consumption reduction, but it has limited applications in the disposing of the solvents that contain water, phosgene and HCl simultaneously.

Patent document CN101326495A describes a method for dehydrating organic solvent by a molecular sieve. For organic solvents, the water content in the ethanol is removed by molecular sieve bed. In said method, the cost for regenerating molecular sieve is very high, and phosgene, HCl and iron component cannot be removed simultaneously, and the color number of the solvents cannot be decreased effectively.

Patent document CN1903990A describes an oil deacidification adsorbent and its preparation method, wherein active clay and inorganic alkaline material are used for oil deacidification after mixing. When said adsorbent is used directly to the removal of water content in organic solvents, local overheating, high pressure drop and channeling would happen, and it has limited effect to the removal of phosgene and hydrogen chloride and to the removal of colored substances in the solvents.

The solvent refining methods described in the above documents are mainly through azeotropic rectification, molecular sieve treatment and inorganic alkaline substances to remove the water content in the solvents, the cost of treatment is high, and the requirement for the content of water in the solvents is high (it is required that the content is lower than 100 ppm), at the same time, the effect of lightening the color of the solvents is poor and may generate local overheat and channeling. It has not been reported a process method that can treat the water content, the iron component, the phosgene and the hydrogen chloride in the solvents simultaneously and can reduce the color number of the solvents used during the manufacture of isocyanates. Therefore, because of the characters of the system during the process of preparation of isocyanates by the phosgene method, the method that can rapidly dispose the fresh solvents with high water content, high iron content and high color number and the solvents with high water content, high iron content, high phosgene content, high hydrogen chloride content and high color number generated during the process of startup and shutdown of devices that are overhauled.

In the prior art, the technology to dispose the solvents with high water content, high iron content, high phosgene content, high hydrogen chloride content and high color number generated during the process of manufacturing isocyanates by salt or just alkaline desiccant cannot remove all the impurities in the solvents, and the content of water in the solvents will only be changed to about 150 ppm, there's not effect of removing the iron component and the colored substances, the phosgene and the hydrogen chloride in the solvents will only be changed to about 500 ppm, and the disposed solvents cannot be used in the process of manufacturing isocyanates.

SUMMARY OF THE INVENTION

The present invention aims to provide a device for refining the solvents generated in the preparation of isocyanates by the phosgene method, and a method of using said device to refine the solvents. By the device and method of the present invention, the water content, the iron component, the phosgene and the hydrogen chloride and the colored substances can be removed rapidly from the solvents to be refined, the technological process is simple, the production cost can be effectively decreased, and the pollution emission and the consumption of the solvents can be reduced.

In order to achieve the above purposes, in one aspect, the present invention provides a device used for refining the solvents generated in the preparation of isocyanates by the phosgene method.

Said device is a multistage absorption tower comprising a support packing section at the bottom, a packing absorbing section in the middle, and a support packing section on top from bottom to top; the packing absorbing section in the middle comprises N absorbing layers, and N is an integer from 3 to 8, preferably N is an integer from 4 to 6; from the first absorbing layer to the Nth absorbing layer, the layers are arranged from bottom to top; from the first absorbing layer to the (N−1)th absorbing layer, each layer of these layers is composed of an upper liquid distributing device that connects an external feeding pipe and a lower absorbing packing layer; the Nth absorbing layer only comprises an absorbing packing layer; the absorbing packing layer of every of the absorbing layers is formed by the uniform mixing of desiccants and adsorbents; solvents to be refined enter the multistage absorption tower from the external feeding pipe, the refined solvents are obtained from the top of the tower, and the waste solutions, which are the desiccant solutions that absorb water content, iron component, phosgene and hydrogen chloride, are obtained from the bottom of the tower.

The liquid distributing device of the present invention can be any liquid distributor known to those skilled in the art. The solvents to be refined are distributed uniformly to the corresponding absorbing packing layer of every of the absorbing layers to enhance the contact of the solvents to the desiccants and the adsorbents, and to increase the treatment effect, preventing the generation of channeling. For example, the liquid distributor comprises but is not limited to nozzle type, slot type, double-deck-pipe type of liquid distributer.

The weight ratio of the desiccants to the adsorbents of the absorbing packing layer of the first absorbing layer of the present invention is 1:1-5:1, preferably 2:1-4:1, and the desiccants represent 4-15% of the weight of all the desiccants in the multistage absorption tower, preferably 5-10%; the weight ratio of the desiccants to the adsorbents of the absorbing packing layer of the Nth absorbing layer is 5:1-12:1, preferably 6:1-10:1, and the desiccants represent 4-15% of the weight of all the desiccants in the multistage absorbing tower, preferably 5-10%; the weight ratio of the desiccants to the adsorbents of every of the absorbing packing layer of the second absorbing layer to the (N−1)th absorbing layer is 5:1-15:1, preferably 6:1-10:1, and the desiccants of every of the absorbing packing layers represent 15-92% of the weight of all the desiccants in the multistage absorption tower, preferably 20-45%.

The desiccants of the present invention are alkaline desiccants, which are selected from one or two or more of calcium oxide, sodium hydroxide and potassium hydroxide, preferably sodium hydroxide; the BET specific surface area of the desiccants is 1500-4500 $m^2/g$, preferably 2500-4000 $m^2/g$, to guarantee the sufficient contact with the solvents to be refined; the average particle size of the desiccants is 0.5-10 μm, preferably 1.5 μm; the mechanical strength of the desiccants is 85-99%, preferably 90-98%, to guarantee that the service life of the desiccant is long enough during the refining process.

The adsorbents of the present invention adopt macroporous resin adsorbents or activated carbon that both can absorb the colored substances in the solvents to be refined; the macroporous resin adsorbents are selected from one or two or more of nonpolar macroporous adsorption resins of styrene polymer and nonpolar macroporous adsorption resins of divinylbenzene polymer, preferably D101 (for example, commercially available from Xian Lan Xiao Science and Technology Ltd.), LX-60 (for example, commercially available from Xian Lan Xiao Science and Technology Ltd.) and LX-20 (for example, commercially available from Xian Lan Xiao Science and Technology Ltd.); the activated carbon is preferably coconut shell activated carbon (for example, commercially available from Chengde Jing Da Activated Carbon Manufacturing Co., Ltd); the BET specific surface area of said adsorbents is 2500-5000 $m^2/g$, preferably 3000-4500 $m^2/g$; the pore size of mesoporous of said adsorbents is 2-10 nm, preferably 2-5 nm; the mechanical strength of said adsorbents is 85-98%, preferably 90-95%.

The macroporous resin adsorbents or the activated carbon of the present invention can form van der Waals force with the iron ion in the solvents to be refined, and effectively adsorb the iron component in the solvents to be refined.

The support packings of the support packing section on top and the support packing section at the bottom are selected from one or two or more of gravels, molecular sieves and activated carbon, preferably molecular sieves, such as 3A type molecular sieve, 5A type molecular sieve and/or 10A type molecular sieve, more preferably 3A type molecular sieve.

The weight of the support packings in the support packing section on top and the weight of the support packings in the support packing section at the bottom are the same, and the weight ratio of the support packings in the support packing section on top to all the desiccants in the multistage absorption tower is 1:20-1:3, preferably 1:15-1:5.

According to one aspect of the present invention, the present invention provides a method for refining the solvents generated in the preparation of isocyanates by the phosgene method, and said method is achieved by the above mentioned multistage absorption tower provided according to the first aspect of the present invention.

Furthermore, according to the method of the present invention, when the multistage absorption tower is used to dispose the solvents to be refined, the ratio of the volume flow rate of the total feed rate of the solvents to be refined to the total weight of all the desiccants and the adsorbents in the multistage absorption tower is 1:200-1:600 m³/kg/h, preferably 1:300-1:500 m³/kg/h.

Preferably, in the method of the present invention, the feeding mode of the solvents to be refined in the multistage absorption tower is a multistage feeding mode, wherein the feeding volume of the external feeding pipe of the first absorbing layer represents 1/15-1/3, preferably 1/10-1/5 of the total feeding volume of the solvents to be refined, the feeding amount of the external feeding pipe of the (N−1)th absorbing layer represents 1/15-1/3, preferably 1/10-1/5 of the total feeding volume of the solvents to be refined, and the feeding amount of the external feeding pipe of every of the absorbing layers, from the second absorbing layer to the (N−2)th absorbing layer, represents 1/15-4/5, preferably 1/10-7/10 of the total feeding amount of the solvents to be refined.

In such multistage feeding mode, the solvents to be refined enter the multistage absorption tower through several flows, which can effectively disperse the heat release after the desiccants absorbing water, phosgene and hydrogen chloride, and meanwhile the desiccant solutions that absorbs water, phosgene and hydrogen chloride discharge from the bottom of the multistage absorption tower and rapidly bring the heat out, thus avoiding local overheat caused by the heat release by the desiccants which absorbs water, phosgene and hydrogen chloride. In addition, the solvents to be refined enter the multistage absorption tower through several flows which avoid a too large flow caused by a single flow that enters the absorption tower, decreasing the initial channeling, and the solvents to be refined are distributed uniformly to the absorbing packing layer of every of the absorbing layers by the liquid distributer, thus effectively avoiding channeling.

According to the method of the present invention, as the multistage absorption tower uses multiple-layer design, with the solvents to be refined entering into the tower through several flows, thus avoiding the problem of nonuniform water absorption of the desiccants owing to low water absorption of the desiccants on the top of the tower but saturation of water absorption of the desiccants at the bottom of the tower, which is caused by a single flow that enters into the tower; meanwhile, because the flow rate of the flow at the bottom of the tower is large, the residence time is long, and the desiccants at the bottom of the tower are plentiful, these are beneficial to the removal of water content, phosgene, hydrogen chloride, iron component and colored substances in the solvents.

According to the method of the present invention, the adsorbents that presents in a specific weight ratio are also used as a diluent for the desiccants, decreasing the contact cohesive force between the desiccants after absorbing water. Meanwhile, the solution of the desiccants after absorbing water are discharged through the bottom of the multistage absorption tower, and effectively prevent the desiccants from hardening.

Preferably, according to the method of the present invention, the residence time of the solvents to be refined in the multistage absorption tower is 0.25-8 hrs, preferably 2-4 hrs.

Preferably, according to the method of the present invention, the refined solvents of the present invention partially reflux and enter into the multistage absorption tower after mixing with the solvents to be refined, and the reflux ratio is 0.5-4, preferably 1-3.

Preferably, according to the method of the present invention, the pressure drop between the external feeding pipe of the first absorbing layer of the multistage absorption tower and the outlet on top of the tower is 5-40 kPa, preferably 10-25 kPa.

According to the present invention, said solvents to be refined are the waste solvents that contains impurities generated during the preparation of isocyanates by the phosgene method or the fresh solvents that should be added to the reaction system during preparation of isocyanates because of the consumption of solvents, and the content of water, iron and the color number in the fresh solvents fail to reach standards; the solvents are selected from one or two or more of o-dichlorobenzene, chlorobenzene and toluene. The content of water in the solvents to be refined is 150-600 ppm, preferably 200-300 ppm; the content of iron component is 40-300 ppm, preferably 50-200 ppm; the content of phosgene and hydrogen chloride is 0-10000 ppm, preferably 0-5000 ppm; the Pt—Co color number is 30-100, preferably 40-80; the content of water in the refined solvents is ≤50 ppm, the content of iron component is ≤5 ppm, the content of phosgene and hydrogen chloride is ≤20 ppm, and Pt—Co color number is ≤20.

The waste solvents after refinement of the present invention is preferably recycled as the solvents for the preparation of isocyanates by the phosgene method.

The contents of iron component in the present invention are all calculated by the contents of iron atoms.

Compared with prior art, using the method and device of the present invention can obtain the following benefits:

(1) uniform mixing of adsorbents and desiccants, effectively prevents the desiccants absorbing water from hardening, prevents local overheat and channeling caused by the heat release of the desiccant absorbing water, phosgene and hydrogen chloride, and effectively decreases the pressure drop at the same time.

(2) the content of water in the solvents to be refined can be removed rapidly to a very low level (≤50 ppm), the content of iron component can be decreased to a very low level 5 ppm), phosgene and hydrogen chloride entrained in the solvents are removed to a very low level (≤20 ppm), the Pt—Co color number of the solvents is decreased (≤20), and the L color of isocyanates is increased; the effect of treatment is obvious, resources are recovered and utilized, and the corrosion of devices are reduced.

(3) solving the problem of higher energy cost and higher requirement of the amount of steam for removing the small amount of water, phosgene and hydrogen chloride in the solvents by rectification process during the process for preparation of isocyanates by the phosgene method at present. The production technological process is simple, the cost is low, the solvent loss is largely reduced, 100 ton/year of the solvent loss can be reduced for 800 thousand tons of crude MDI produced per year, and the cost of production is decreased.

BRIEF DESCRIPTION OF THE DRAWINGS

FIG. 1 is the schematic diagram of the multistage absorption tower used in examples 1-5 according to the present invention.

DETAILED DESCRIPTION

The present invention will be further illustrated by the following examples, but the present invention is not limited to the following examples. When the detailed experiment conditions for the experiment method are not mentioned in the following examples, the conditions follow the conventional conditions.

In the following examples:

The L color of isocyanates is measured by the L value, a value and b value of the CIE color system known by those skilled in the art;

The content of iron component in the solvents is determined by the content of iron atoms measured at 248.33 nm by atomic absorption emission spectrometer;

The content of water in the solvents is measured by the automatic Karl fischer moisture meter;

The content of phosgene and hydrogen chloride is measured by the reaction of sodium hydroxide with phosgene and hydrogen chloride, then adding silver nitrate and measuring the content of the residual silver ions by automatic potentiometric titrator, and then converting the content of the residual silver ions to the content of phosgene and hydrogen chloride in the solvents;

The coconut shell activated carbon is commercially available from Chengde Jing Da Activated Carbon Manufacturing Company; the macroporous resin D101 is commercially available from Xian Lan Xiao Science and Technology Ltd.

Example 1

The desiccants are sodium hydroxide, the total amount of the desiccants in the absorption tower is 500 kg, the BET specific surface area of the desiccants is 2500 m$^2$/g, the average particle size is 1 μm, and the mechanical strength is 90%; the adsorbents are coconut shell activated carbon, the BET specific surface area is 3000 m$^2$/g, the pore size of the mesoporous is 2 nm, and the mechanical strength is 90%. The support packings on top and bottom of the absorption tower are 3A type molecular sieves, and the total amount is all 50 kg. There are N absorbing layers and N is 4; from the first absorbing layer to the third absorbing layer, each layer of these layers is composed of an upper liquid distributing device that connects an external feeding pipe and a lower absorbing packing layer; the weight ratio of the desiccants to the adsorbents of the absorbing packing layer of the first absorbing layer is 2:1, and the desiccants represents 5% of the weight of all the desiccants in the multistage absorption tower; the weight ratio of the desiccants to the adsorbents of the absorbing packing layer of every of the second and third absorbing layer is 10:1, and the desiccants of the absorbing packing layer of every of the second and third absorbing layers represents 45% of the weight of all the desiccants in the multistage absorption tower; the weight ratio of the desiccants to the adsorbents of the absorbing packing layer of the fourth absorbing layer is 10:1, and the desiccants represents 5% of the weight of all the desiccants in the multistage absorption tower. The desiccants and the adsorbents of the absorbing packing layer of every of the absorbing layers are mixed uniformly and then are filled. The pressure drop between the external feeding pipe of the first absorbing layer of the multistage absorbing tower and the outlet on top of the tower is 10 kPa.

The solvent to be refined is the waste chlorobenzene solvent generated during the abnormal startup and shutdown of the MDI manufacturing device, the ratio of the volume flow rate of the total feed rate of the solvent to the total weight of all the desiccants and the adsorbents in the multistage absorption tower is 1:300 m$^3$/kg/h; the feed rate of the external feeding pipe of the first absorbing layer represents 1/5 of the volume of the total feed rate of the solvent to be refined, the feed rate of the external feeding pipe of the second absorbing layer represents 7/10 of the volume of the total feed rate of the solvent to be refined, and the feed rate of the external feeding pipe of the third absorbing layer represents 1/10 of the volume of the total feed rate of the solvent to be refined. The residence time of the solvent to be refined in the multistage absorption tower is 2 hrs, and the reflux ratio of the refined solvent to the solvent to be refined is 1.

The content of water in the solvent to be refined is 300 ppm, the content of iron component is 50 ppm, the content of phosgene and hydrogen chloride is 5000 ppm, and the Co—Pt color number is 40. The analysis results of the refined solvent are shown in table 1. The refined solvent is reused as the MDI manufacturing solvent, the method of manufacturing is referred to the method of manufacturing MDI in the patent document CN1254724A, and the analysis results of the obtained MDI product are shown in table 1.

Example 2

The desiccants are potassium hydroxide, the total amount of the desiccants in the absorption tower is 1000 kg, the BET specific surface area of the desiccants is 3000 m$^2$/g, the average particle size is 3 μm, and the mechanical strength is 95%; the adsorbents are coconut shell activated carbon, the BET specific surface area is 3500 m$^2$/g, the pore size of the mesoporous is 4 nm, the mechanical strength is 93%. The support packings on top and bottom of the absorption tower is 5A type molecular sieves, and the total amount is all 80 kg. There are N absorbing layers and N is five; from the first layer to the fourth layer, each layer of these layers is composed of an upper liquid distributing device that connects an external feeding pipe and a lower absorbing packing layer; the weight ratio of the desiccants to the adsorbents of the absorbing packing layer of the first absorbing layer is 3:1, and the desiccants represents 7% of the weight of all the desiccants in the multistage absorption tower; the weight ratio of the desiccants to the adsorbents of the absorbing packing layer of every of the second, third and fourth absorbing layers is 9:1, the desiccants of the absorbing packing layer of every of the second, third and fourth absorbing layers represents 29% of the weight of all the desiccants in the multistage absorption tower; the weight ratio of the desiccants to the adsorbents of the absorbing packing layer of the fifth absorbing layer is 6:1, and the desiccants represents 6% of the weight of all the desiccants in the multistage absorption tower. The desiccants and the adsorbents of the absorbing packing layer of every of the absorbing layers are mixed uniformly and then are filled. The pressure drop between the external feeding pipe of the first absorbing layer of the multistage absorption tower and the outlet on the top of the tower is 16 kPa.

The solvent to be refined is the waste dichlorobenzene solvent generated during the overhaul of the TDI manufacturing device, the ratio of the volume flow rate of the total feed rate of the solvent to the total weight of all the desiccants and the adsorbents in the multistage absorption tower is 1:400 m$^3$/kg/h; the feed rate of the external feeding pipe of the first absorbing layer represents 1/8 of the volume of the total feed rate of the solvent to be refined, the feed rate of the external feeding pipe of every of the second and third absorbing layers represents 3/8 of the volume of the total feed rate of the solvent to be refined respectively, and the feed rate of the external feeding pipe of the fourth absorbing layer represents 1/8 of the volume of the total feed rate of the solvent to be refined. The residence time of the solvent to be refined in the multistage absorption tower is 3 hrs, and the reflux ratio of the refined solvent to the solvent to be refined is 1.5.

The content of water in the solvent to be refined is 200 ppm, the content of iron component is 150 ppm, the content of phosgene and hydrogen chloride is 4000 ppm, and the Co—Pt color number is 60; the analysis results of the refined solvent are shown in table 1. The refined solvent is reused as the TDI manufacturing solvent, the method of manufacturing is referred to the method of manufacturing TDI in the patent document CN101205199A, and the analysis results of the obtained TDI product are shown in table 1.

Example 3

The desiccants are sodium hydroxide, the total amount of the desiccants in the absorbing tower is 800 kg, the BET specific surface area of the desiccants is 4000 $m^2/g$, the average particle size is 5 μm, and the mechanical strength is 98%; the adsorbents are divinyl benzene polymer based nonpolar macroporous resin—D101, the BET specific surface area is 4500 $m^2/g$, the pore size of the mesoporous is 5 nm, and the mechanical strength is 95%; the support packings on top and bottom of the absorption tower are 10A type molecular sieves, the total amount is all 90 kg. There are N absorbing layers and N is six; from the first layer to the fifth layer, each layer of these layers is composed of an upper liquid distributing device that connects an external feeding pipe and a lower absorbing packing layer; the weight ratio of the desiccants to the adsorbents of the absorbing packing layer of the first absorbing layer is 4:1, and the desiccants represents 10% of the weight of all the desiccants in the multistage absorption tower; the weight ratio of the desiccants to the adsorbents of the absorbing packing layer of every of the second, third, fourth and fifth absorbing layers is 5:1, and the desiccants of the absorbing packing layer of every of the second, third, fourth and fifth absorbing layers represents 20.5% of the weight of all the desiccants in the multistage absorption tower; the weight ratio of the desiccants to the adsorbents of the absorbing packing layer of the sixth absorbing layer is 5:1, and the desiccants represents 8% of the weight of all the desiccants in the multistage absorption tower. The desiccants and the adsorbents of the absorbing packing layer of every of the absorbing layers are mixed uniformly and then are filled. The pressure drop between the external feeding pipe of the first absorbing layer of the multistage absorption tower and the outlet on the top of the tower is 25 kPa.

The solvent to be refined is the fresh chlorobenzene solvent to be added to the HDI manufacturing device, the ratio of the volume flow rate of the total feed rate of the solvent to the total weight of all the desiccants and the adsorbents in the multistage absorption tower is 1:500 $m^3/kg/h$; the feed rate of the external feeding pipe of the first absorbing layer represents ⅕ of the volume of the total feed rate of the solvent to be refined, the feed rates of the external feeding pipe of the second, third and fourth absorbing layers respectively represents ⅕ of the volume of the total feed rate of the solvent to be refined, and the feed rate of the external feeding pipe of the fifth absorbing layer represents ⅕ of the volume of the total feed rate of the solvent to be refined. The residence time of the solvent to be refined in the multistage absorption tower is 4 hrs, and the reflux ratio of the refined solvent to the solvent to be refined is 3.

The content of water in the solvent to be refined is 150 ppm, the content of iron component is 200 ppm, the content of phosgene and hydrogen chloride is 0 ppm, and the Co—Pt color number is 80. The analysis results of the refined solvent are shown in table 1. The refined solvent is reused as the HDI manufacturing solvent, the method of manufacturing is referred to the method of manufacturing HDI in the patent document CN101429139A, and the analysis results of the obtained HDI product are shown in table 1.

Example 4

The desiccants are calcium oxide, the total amount of the desiccants in the absorbing tower is 1200 kg, the BET specific surface area of the desiccants is 4200 $m^2/g$, the average particle size is 4.5 μm, and the mechanical strength is 95%; the adsorbents are nonpolar macroporous adsorption resin of styrene polymer—LX-60, the BET specific surface area is 4800 $m^2/g$, the pore size of the mesoporous is 4.5 nm, and the mechanical strength is 93%. The support packings on top and bottom of the absorption tower is 5A type molecular sieves, and the total amount is all 120 kg. There are N absorbing layers and N is six; from the first layer to the fifth layer, each layer of these layers is composed of an upper liquid distributing device that connects an external feeding pipe and a lower absorbing packing layer; the weight ratio of the desiccants to the adsorbents of the absorbing packing layer of the first absorbing layer is 4:1, and the desiccants represents 10% of the weight of all the desiccants in the multistage absorption tower; the weight ratio of the desiccants to the adsorbents of the absorbing packing layer of every of the second, third, fourth and fifth absorbing layers is 5:1, and the desiccants of the absorbing packing layer of every of the second, third, fourth and fifth absorbing layers represents 20.5% of the weight of all the desiccants in the multistage absorption tower; the weight ratio of the desiccants to the adsorbents of the absorbing packing layer of the sixth absorbing layer is 5:1, and the desiccants represents 8% of the weight of all the desiccants in the multistage absorption tower. The desiccants and the adsorbents of the absorbing packing layer of every of the absorbing layers are mixed uniformly and then are filled. The pressure drop between the external feeding pipe of the first absorbing layer of the multistage absorption tower and the outlet on the top of the tower is 25 kPa.

The solvent to be refined is the fresh toluene solvent to be added to the MDI manufacturing device, the ratio of the volume flow rate of the total feed rate of the solvent to the total weight of all the desiccants and the adsorbents in the multistage absorption tower is 1:400 $m^3/kg/h$; the feed rate of the external feeding pipe of the first absorbing layer represents ⅕ of the volume of the total feed rate of the solvent to be refined, the feed rates of the external feeding pipe of the second, third and fourth absorbing layers respectively represents ⅕ of the volume of the total feed rate of the solvent to be refined, and the feed rate of the external feeding pipe of the fifth absorbing layer represents ⅕ of the volume of the total feed rate of the solvent to be refined. The residence time of the solvent to be refined in the multistage absorption tower is 3.5 hrs, and the reflux ratio of the refined solvent to the solvent to be refined is 2.

The content of water in the solvent to be refined is 250 ppm, the content of iron component is 120 ppm, the content of phosgene and hydrogen chloride is 0 ppm, and the Co—Pt color number is 60. The analysis results of the refined solvent are shown in table 1. The refined solvent is reused as the MDI manufacturing solvent, the method of manufacturing is referred to the method of manufacturing MDI in the patent document CN1254724A, and the analysis results of the obtained MDI product are shown in table 1.

Example 5

The desiccants are potassium hydroxide, the total amount of the desiccants in the absorption tower is 900 kg, the BET specific surface area of the desiccants is 3200 m$^2$/g, the average particle size is 5 μm, and the mechanical strength is 95%; the adsorbents is nonpolar macroporous absorption resin of styrene polymer—LX-20, the BET specific surface area is 5000 m$^2$/g, the pore size of the mesoporous is 4 nm, and the mechanical strength is 95%; the support packings on top and bottom of the absorption tower is 3A type molecular sieves, and the total amount is all 90 kg. There are N absorbing layers and N is five; from the first layer to the fourth layer, each layer of these layers is composed of an upper liquid distributing device that connects an external feeding pipe and a lower absorbing packing layer; the weight ratio of the desiccants to the adsorbents of the absorbing packing layer of the first absorbing layer is 3:1, and the desiccants represents 7% of the weight of all the desiccants in the multistage absorption tower; the weight ratio of the desiccants to the adsorbents of the absorbing packing layer of every of the second, third and fourth absorbing layers is 9:1, and the desiccants of the absorbing packing layer of every of the second, third and fourth absorbing layers represents 29% of the weight of all the desiccants in the multistage absorption tower; the weight ratio of the desiccants to the adsorbents of the absorbing packing layer of the fifth absorbing layer is 6:1, and the desiccants represents 6% of the weight of all the desiccants in the multistage absorption tower. The desiccants and the adsorbents of the absorbing packing layer of every of the absorbing layers are mixed uniformly and then are filled. The pressure drop between the external feeding pipe of the first absorbing layer of the multistage absorption tower and the outlet on the top of the tower is 20 kPa.

The solvent to be refined is the waste chlorobenzene solvent generated during the overhaul of the TDI manufacturing device, the ratio of the volume flow rate of the total feed rate of the solvent to the total weight of all the desiccants and the adsorbents in the multistage absorption tower is 1:420 m$^3$/kg/h; the feed rate of the external feeding pipe of the first absorbing layer represents ⅛of the volume of the total feed rate of the solvent to be refined, the feed rate of the external feeding pipe of every of the second and the third absorbing layers represents ⅜of the volume of the total feed rate of the solvent to be refined respectively, and the feed rate of the external feeding pipe of the fourth absorbing layer represents ⅛of the volume of the total feed rate of the solvent to be refined. The residence time of the solvent to be refined in the multistage absorption tower is 4 hrs, and the reflux ratio of the refined solvent to the solvent to be refined is 1.5.

The content of water in the solvent to be refined is 260 ppm, the content of iron component is 180 ppm, the content of phosgene and hydrogen chloride is 3000 ppm, and the Co—Pt color number is 50; the analysis results of the refined solvent are shown in table 1. The refined solvent is reused as the TDI manufacturing solvent, the method of manufacturing is referred to the method of manufacturing TDI in the patent document CN101205199A, and the analysis results of the obtained TDI product are shown in table 1.

Comparative Example 1

The waste chlorobenzene solvent is processed by a vacuum distillation column. The operation pressure of the vacuum distillation column is 40 kpa, the flux ratio is 2:1, the temperature of the bottom of the column is controlled at 100-105° C., and the temperature of the top of the column is controlled at 60-65° C.

The solvent to be refined is the waste chlorobenzene solvent generated during the abnormal startup and shutdown of the MDI manufacturing device, wherein the content of water is 300 ppm, the content of iron component is 50 ppm, the content of phosgene and hydrogen chloride is 5000 ppm, and the Co—Pt color number is 60; the analysis results of the refined solvent are shown in table 1. The refined solvent is reused as the MDI manufacturing solvent, the method of manufacturing is referred to the method of manufacturing MDI in the patent document CN1254724A, and the analysis results of the obtained MDI product are shown in table 1.

Comparative Example 2

The waste dichlorobenzene solvent is processed by azeotropic rectification tower, and the entrainer is tetrahydrofuran; the entrainer and the solvent to be refined are added to the bottom of the azeotropic rectification tower together, the weight ratio of the entrainer and the solvent to be refined is 10:1, the reflux ratio during operation is 2, the operation pressure of the azeotropic rectification tower is 101.3 kpa, the temperature of the top of the tower is controlled at 65-69° C., and the temperature of the bottom of the tower is controlled at 138-140° C.

The solvent to be refined is the waste dichlorobenzene solvent generated during the operation of the solvent after the overhaul of the TDI manufacturing device, wherein the content of water is 280 ppm, the content of iron component is 45 ppm, the content of phosgene and hydrogen chloride is 4800 ppm, and the Co—Pt color number is 55; the analysis results of the refined solvent are shown in table 1. The refined solvent is reused as the TDI manufacturing solvent, the method of manufacturing is referred to the method of manufacturing TDI in the patent document CN101205199A, and the analysis results of the obtained TDI product are shown in table 1.

TABLE 1

Analysis results

| | Analysis indicators of the refined solvent | | | | | L color of the product |
|---|---|---|---|---|---|---|
| | The content of water (ppm) | The content of iron component (ppm) | Phosgene + hydrogen chloride (ppm) | Po-Co color | Recovery Rate | |
| Example 1 | 47 | 1.5 | 18 | 5 | 99.8% | 92 |
| Example 2 | 39 | 2.7 | 14 | 15 | 99.6% | 98 |
| Example 3 | 29 | 2.2 | 0 | 20 | 99.7% | 95 |
| Example 4 | 45 | 1.8 | 0 | 5 | 99.9% | 90 |
| Example 5 | 35 | 2.4 | 8 | 10 | 99.5% | 93 |
| Comparative example 1 | 115 | 9.9 | 89 | 45 | 89% | 82 |
| Comparative example 2 | 108 | 8.5 | 82 | 40 | 90% | 85 |

The invention claimed is:

1. A method for refining solvents generated in the preparation of isocyanates by the phosgene method, comprising treating the solvents to be refined with a multistage absorption tower comprising a support packing section at the bottom, a packing absorbing section in the middle and a support packing section on the top from bottom to top, wherein the packing absorption section in the middle comprises N absorbing layers, and N is an integer from 3 to 8; from the first absorbing layer to the Nth absorbing layer, the layers are arranged from bottom to top; from the first absorbing layer to the (N−1)th absorbing layer, each layer of these layers is composed of an upper liquid distributing device that connects an external feeding pipe and a lower absorbing packing layer; and the absorbing packing layer of every of the absorbing layers is formed by the uniform mixing of desiccants and adsorbents.

2. The method according to claim 1, wherein the weight ratio of the desiccants to the adsorbents of the absorbing packing layer of the first absorbing layer is 1:1-5:1, and the desiccants represent 4-15% of the weight of all the desiccants in the multistage absorption tower; the weight ratio of the desiccants to the adsorbents of the absorbing packing layer of the Nth absorbing layer is 5:1-12:1, and the desiccants represent 4-15% of the weight of all the desiccants in the multistage absorption tower; and the weight ratio of the desiccants to the adsorbents of the absorbing packing layer of every of the second absorbing layer to the (N−1)th absorbing layer is 5:1-15:1, and the desiccants of every of the absorbing packing layers represent 15-92% of the weight of all the desiccants in the multistage absorption tower.

3. The method according to claim 1, wherein the desiccants are alkaline desiccants, which are selected from the group consisting of calcium oxide, sodium hydroxide, potassium hydroxide, and a mixture of two or more thereof; the BET specific surface area of the desiccants is 1500-4500 m$^2$/g; the average particle size is 0.5-10 μm; and the mechanical strength is 85-99%.

4. The method according to claim 1, wherein the adsorbents are macroporous resin adsorbents or activated carbon; the macroporous resin adsorbents are selected from the group consisting of nonpolar macroporous adsorption resins of styrene polymer, nonpolar macroporous adsorption resins of divinylbenzene polymer, and a mixture of two or more thereof; the BET specific surface area of the adsorbents is 2500-5000 m$^2$/g; the pore size of mesoporous is 2-10 nm; and the mechanical strength is 85-98%.

5. The method according to claim 1, wherein the support packings of the support packing section on top and the support packing section at the bottom are selected from the group consisting of gravels, molecular sieves, activated carbon, and a mixture of two or more thereof; the weight of the support packings in the support packing section on top and the weight of the support packings in the support packing section at the bottom are the same; and the weight ratio of the support packings in the support packing section on top to all the desiccants in the multistage absorption tower is 1:20-1:3.

6. The method according to claim 1, wherein the ratio of the volume flow rate of the total feed rate of the solvents to be refined to the total weight of all the desiccants and the adsorbents in the multistage absorption tower is 1:200-1:600 m$^3$/kg/h.

7. The method according to claim 6, wherein the feeding volume of the external feeding pipe of the first absorbing layer represents 1/15-1/3 of, the total feeding volume of the solvents to be refined, the feeding amount of the external feeding pipe of the (N−1)th absorbing layer represents 1/15-1/3 of the total feeding volume of the solvents to be refined, and the feeding amount of the external feeding pipe of every of the absorbing layers, from the second absorbing layer to the (N−2)th absorbing layer, represents 1/15-4/5 of the total feeding amount of the solvents to be refined.

8. The method according to claim 7, wherein the residence time of the solvents to be refined in the multistage absorption tower is 0.25-8 hrs.

9. The method according to claim 6, wherein the refined solvents partially reflux and enter into the multistage absorption tower after mixing with the solvents to be refined, and the reflux ratio is 0.5-4; and the pressure drop between the external feeding pipe of the first absorbing layer of the multistage absorption tower and the outlet on top of the tower is 5-40 kPa.

10. The method according to claim 1, wherein the solvents to be refined are the waste solvents that contains impurities generated during the preparation of isocyanates by the phosgene method or the fresh solvents that should be added to the reaction system during preparation of isocyanates because of the consumption of solvents, and the content of water, iron and the color number in the fresh solvents fail to reach standards; the solvents are selected from the group consisting of o-dichlorobenzene, chlorobenzene, toluene, and a mixture of two or more thereof; the content of water in the solvents to be refined is 150-600 ppm; the content of iron component is 40-300 ppm; the content of phosgene and hydrogen chloride is 0-10000 ppm; the Pt—Co color number is 30-100; the content of water in the refined solvents is ≤50 ppm; the content of iron component is ≤5 ppm; the content of phosgene and hydrogen chloride is ≤20 ppm; and Pt—Co color number is ≤20.

11. A multistage absorption tower used for refining solvents generated in the preparation of isocyanates by the phosgene method, comprising:
a support packing section at the bottom;
a packing absorbing section in the middle; and
a support packing section on top from bottom to top;
wherein the packing absorbing section in the middle comprises N absorbing layers, and N is an integer from 3 to 8; from the first absorbing layer to the Nth absorbing layer, the layers are arranged from bottom to top; from the first layer to the (N−1)th absorbing layer, each layer of these layers is composed of an upper liquid distributing device that connects an external feeding pipe and a lower absorbing packing layer; and the absorbing packing layer of every of the absorbing layers is formed by the uniform mixing of desiccants and adsorbents.

12. The multistage absorption tower according to claim 11, wherein the weight ratio of the desiccants to the adsorbents of the absorbing packing layer of the first absorbing layer is 1:1-5:1, and the desiccants represent 4-15% of the weight of all the desiccants in the multistage absorption tower; the weight ratio of the desiccants to the adsorbents of the absorbing packing layer of the Nth absorbing layer is 5:1-12:1, and the desiccants represent 4-15% of the weight of all the desiccants in the multistage absorption tower; and the weight ratio of the desiccants to the adsorbents of the absorbing packing layer of every of the second absorbing layer to the (N−1)th absorbing layer is 5:1-15:1, and the desiccants of every of the absorbing packing layers represent 15-92% of the weight of all the desiccants in the multistage absorption tower.

13. The multistage absorbing tower according to claim 11, wherein the desiccants are alkaline desiccant, which are selected from the group consisting of calcium oxide, sodium hydroxide, potassium hydroxide, and a mixture of two or more thereof; the BET specific surface area of the desiccants is 1500-4500 m$^2$/g; the average particle size is 0.5-10μm; and the mechanical strength is 85-99%.

14. The multistage absorbing tower according to claim 11, wherein the adsorbents are macroporous resin adsorbents or activated carbon; the macroporous resin adsorbents are selected from the group consisting of nonpolar macroporous adsorption resins of styrene polymer, nonpolar macroporous adsorption resins of divinylbenzene polymer, and a mixture of two or more thereof; the BET specific surface area of the adsorbents is 2500-5000 $m^2/g$; the pore size of mesoporous is 2-10 nm, and the mechanical strength is 85-98%.

15. The multistage absorbing tower according to claim 11, wherein the support packings of the support packing section on top and the support packing section at the bottom are selected from the group consisting of gravels, molecular sieves, activated carbon, and a mixture of two or more thereof; the weight of the support packings in the support packing section on top and the weight of the support packing in the support packing section at the bottom are the same; and the weight ratio of the support packing in the support packing section on top to all the desiccants in the multistage absorption tower is 1:20-1:3.

16. The method according to claim 1, where N is an integer from 4-6.

17. The method according to claim 2, wherein the weight ratio of the desiccants to the adsorbents of the absorbing packing layer of the first absorbing layer is 2:1-4:1, and the desiccants represent 5-10% of the weight of all the desiccants in the multistage absorption tower; the weight ratio of the desiccants to the adsorbents of the absorbing packing layer of the Nth absorbing layer is 6:1-10:1, and the desiccants represent 5-10% of the weight of all the desiccants in the multistage absorption tower; and the weight ratio of the desiccants to the adsorbents of the absorbing packing layer of every of the second absorbing layer to the (N−1)th absorbing layer is 6:1-10:1, and the desiccants of every of the absorbing packing layers represent 20-45% of the weight of all the desiccants in the multistage absorption tower.

18. The method according to claim 6, wherein the ratio of the volume flow rate of the total feed rate of the solvents to be refined to the total weight of all the desiccants and the adsorbents in the multistage absorption tower is 1:300-1:500 $m^3/kg/h$.

19. The method according to claim 7, wherein the feeding volume of the external feeding pipe of the first absorbing layer represents $1/10$-$1/5$ of the total feeding volume of the solvents to be refined, the feeding amount of the external feeding pipe of the (N−1)th absorbing layer represents $1/10$-$1/5$ of the total feeding volume of the solvents to be refined, and the feeding amount of the external feeding pipe of every of the absorbing layers, from the second absorbing layer to the (N−2)th absorbing layer, represents $1/10$-$7/100$ of the total feeding amount of the solvents to be refined.

20. The method according to claim 9, wherein the reflux ratio is 1-3; and the pressure drop between the external feeding pipe of the first absorbing layer of the multistage absorption tower and the outlet on top of the tower is 10-25 kPa.

21. The multistage absorption tower according to claim 11, wherein N is an integer from 4 to 6.

22. The multistage absorption tower according to claim 12, wherein the weight ratio of the desiccants to the adsorbents of the absorbing packing layer of the first absorbing layer is 2:1-4:1, and the desiccants represent 5-10% of the weight of all the desiccants in the multistage absorption tower; the weight ratio of the desiccants to the adsorbents of the absorbing packing layer of the Nth absorbing layer is 6:1-10:1, and the desiccants represent 5-10% of the weight of all the desiccants in the multistage absorption tower; and the weight ratio of the desiccants to the adsorbents of the absorbing packing layer of every of the second absorbing layer to the (N−1)th absorbing layer is 6:1-10:1, and the desiccants of every of the absorbing packing layers represent 20-45% of the weight of all the desiccants in the multistage absorption tower.

* * * * *